(12) United States Patent
Kim et al.

(10) Patent No.: US 11,359,965 B2
(45) Date of Patent: Jun. 14, 2022

(54) APPARATUS AND METHOD FOR ESTIMATING TARGET COMPONENT

(71) Applicant: SAMSUNG ELECTRONICS CO., LTD., Suwon-si (KR)

(72) Inventors: Yoon Jae Kim, Seoul (KR); Sang Kyu Kim, Yongin-si (KR); Hyun Seok Moon, Hwaseong-si (KR); Jin Young Park, Hwaseong-si (KR); Sung Mo Ahn, Yongin-si (KR); Kun Sun Eom, Yongin-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/217,465

(22) Filed: Mar. 30, 2021

(65) Prior Publication Data
US 2022/0107220 A1    Apr. 7, 2022

(30) Foreign Application Priority Data
Oct. 5, 2020    (KR) .................. 10-2020-0127933

(51) Int. Cl.
   *G01J 3/28*    (2006.01)
   *G01J 3/02*    (2006.01)
   *G01N 33/483*    (2006.01)

(52) U.S. Cl.
   CPC .............. *G01J 3/28* (2013.01); *G01J 3/027* (2013.01); *G01N 33/483* (2013.01)

(58) Field of Classification Search
   CPC .. G01J 1/44; G01J 1/42; G01J 1/4214; H03M 1/00; H03M 2201/02
   USPC ........................................................ 356/326
   See application file for complete search history.

(56) References Cited

U.S. PATENT DOCUMENTS

| | | | |
|---|---|---|---|
| 5,725,480 | A | 3/1998 | Oosta et al. |
| 8,260,402 | B2 | 9/2012 | Ermakov et al. |
| 10,653,343 | B2 | 5/2020 | Dhawan |
| 10,883,876 | B2 | 1/2021 | Ahn et al. |

(Continued)

FOREIGN PATENT DOCUMENTS

| | | |
|---|---|---|
| JP | 2001-161664 A | 6/2001 |
| JP | 2011-087907 A | 5/2011 |

(Continued)

OTHER PUBLICATIONS

Communication dated Dec. 14, 2021 issued by the European Intellectual Property Office in counterpart European Application No. 21185830.3.

(Continued)

*Primary Examiner* — Md M Rahman
(74) *Attorney, Agent, or Firm* — Sughrue Mion, PLLC

(57) ABSTRACT

The present disclosure relates to an apparatus for non-invasively estimating a target component value based on a light spectrum. The apparatus for estimating the target component value may include a sensor configured to obtain a spectrum of light scattered or reflected from an object, and a processor configured to correct a first reflectance value of the spectrum based on a melanin index; obtain a second reflectance value based on correcting the first reflectance value; convert the second reflectance value into an absorbance value; estimate the target component value based on the absorbance value; and correct the target component value based on a hemoglobin index.

30 Claims, 12 Drawing Sheets

(56) References Cited

U.S. PATENT DOCUMENTS

| | | |
|---|---|---|
| 2003/0032064 A1 | 2/2003 | Soller et al. |
| 2010/0179435 A1 | 7/2010 | Sharifzadeh et al. |
| 2012/0330164 A1 | 12/2012 | Ermakov et al. |
| 2013/0289414 A1 | 10/2013 | Adibnazari et al. |
| 2016/0022181 A1 | 1/2016 | Valsan et al. |
| 2020/0029873 A1 | 1/2020 | Park et al. |
| 2020/0155081 A1 | 5/2020 | Seo et al. |

FOREIGN PATENT DOCUMENTS

| | | |
|---|---|---|
| JP | 2015-023953 A | 2/2015 |
| KR | 10-2011-0038020 A | 4/2011 |
| KR | 10-2018-0114458 A | 10/2018 |
| KR | 10-2020-0012597 A | 2/2020 |
| KR | 10-2020-0045737 A | 5/2020 |

OTHER PUBLICATIONS

Olusola O. Soyemi et al., "Skin Color Correction for Tissue Spectroscopy: Demonstration of a Novel Approach with Tissue-Mimicking Phantoms", Applied Spectroscopy, vol. 59, No. 2, 8 pages total, Feb. 2005, XP002648657.

Ian D. Stephen et al., "Carotenoid and melanin pigment coloration affect perceived human health", Evolution and Human Behavior, 2011, vol. 32, pp. 216-227 (12 pages total).

U.S. Appl. No. 16/950,258, Pending, filed Nov. 17, 2020.

U.S. Appl. No. 17/077,700, Pending, filed Oct. 22, 2020.

APPARATUS AND METHOD FOR ESTIMATING TARGET COMPONENT

CROSS-REFERENCE TO RELATED APPLICATION(S)

This application is based on and claims priority under 35 U.S.C. § 119 to Korean Patent Application No. 10-2020-0127933, filed on Oct. 5, 2020 in the Korean Intellectual Property Office, the disclosure of which is incorporated by reference herein in its entirety.

BACKGROUND

1. Field

The disclosure relates to an apparatus and method for non-invasively estimating a target component by using a spectrum obtained from an object.

2. Description of Related Art

Recently, research has been conducted on methods to non-invasively estimate components, such as blood glucose and carotenoid, by using Raman spectroscopy or Near-infrared spectroscopy. Skin color is generally determined by factors such as hemoglobin, carotene, melanin, and the like. Particularly, melanin, which absorbs substantial amounts of light, causes a reduction in performance, such as a signal to noise ratio, and the like, of a spectrum-based sensor. That is, the effects of hemoglobin and melanin pigment, responsible for skin color, are reflected in the absorbance spectrum, such that accuracy in measuring components, such as carotenoid, from people of various skin colors may be reduced.

SUMMARY

According to an aspect of an example embodiment, an apparatus for estimating a target component value may include a sensor configured to obtain a spectrum of light scattered or reflected from an object, and a processor configured to correct a first reflectance value of the spectrum based on a melanin index; obtain a second reflectance value based on correcting the first reflectance value; convert the second reflectance value into an absorbance value; estimate the target component value based on the absorbance value; and correct the target component value based on a hemoglobin index.

The processor may calculate a melanin correction value based on the melanin index, a reference melanin index, and a correction ratio; and correct the first reflectance value based on the melanin correction value.

The correction ratio may include a rate of change of the first reflectance value as compared to a change in the melanin index.

The processor may calculate the melanin correction value by multiplying a value, obtained by subtracting the reference melanin index from the melanin index, by a negative of the correction ratio.

The processor may calculate a hemoglobin correction value based on the hemoglobin index, a reference hemoglobin index, and a correction ratio; and correct the target component based on the hemoglobin correction value.

The correction ratio may include a rate of change of a residual, which is a value obtained by subtracting a trend line from the target component value, as compared to a change in the hemoglobin index.

The processor may calculate the hemoglobin correction value by multiplying a value, obtained by subtracting the reference hemoglobin index from the hemoglobin index, by a predetermined ratio, and multiplying the resulting value by the correction ratio.

The sensor may include a light source pail configured to emit light in a predetermined wavelength range onto the object; and a spectrometer configured to split the light scattered or reflected from the object to obtain the spectrum.

The predetermined wavelength range may include a wavelength range of visible light.

The processor may estimate the target component based on absorbance values in a first wavelength range of the predetermined wavelength range.

The processor may convert the first reflectance value into a first absorbance value; and estimate the melanin index and the hemoglobin index based on the first absorbance value.

The processor may estimate the melanin index based on absorbance values in a second wavelength range of the predetermined wavelength range associated with melanin; and estimate the hemoglobin index based on absorbance values in a third wavelength range associated with hemoglobin.

The sensor may include a first light source part configured to emit light in a first wavelength range; a second light source part configured to emit light in a second wavelength range associated with melanin; a third light source part configured to emit light in a third wavelength range associated with hemoglobin; and a detector configured to detect the light scattered or reflected from the object.

The processor may estimate the melanin index by driving the second light source part; estimate the hemoglobin index by driving the third light source part; and obtain the second reflectance value by correcting the first reflectance value of the spectrum, detected by driving the first light source part, based on the melanin index.

The first wavelength range may include a wavelength range of 470 nanometers (nm) to 510 am, the second wavelength range includes a wavelength range of 400 nm to 470 nm, and the third wavelength range includes a wavelength range of 530 nm to 590 nm.

The detector may include one or more of a photo diode, a complementary metal-oxide semiconductor (CMOS) image sensor; and a charge-coupled device (CCD) image sensor.

The target component value may include one or more of a carotenoid value, a blood glucose value, a sugar intake value, a triglyceride value, a cholesterol value, a caloric value, a protein value, an in vivo body fluid value, an in vitro body fluid value, and a uric acid value.

According to an aspect of an example embodiment, an apparatus for estimating a target component value may include a first light source part configured to emit light in a first wavelength range associated with a target component; a second light source part configured to emit light in a second wavelength range associated with melanin; a third light source part configured to emit light in a third wavelength range associated with hemoglobin; a detector configured to detect light, scattered or reflected from the object, in the first wavelength range, the second wavelength range, and the third wavelength range; and a processor configured to convert a first reflectance value of the light in the first wavelength range into a first absorbance value; convert a second reflectance value of the light in the second wavelength range into a second absorbance value; convert a third reflectance value of the light in the third wavelength range into a third absorbance value; and estimate the target component value of the target component, based on the first absorbance value, the second absorbance value, and the third absorbance value.

The processor may sequentially or simultaneously drive the first light source part, the second light source part, and the third light source part.

According to an aspect of an example embodiment, a method of estimating a target component value may include obtaining a spectrum of light scattered or reflected from an object; correcting a first reflectance value of the spectrum based on a melanin index; obtaining a second reflectance value based on correcting the first reflectance value; converting the second reflectance value into an absorbance value; estimating the target component value based on the absorbance value; and correcting the target component value based on a hemoglobin index.

The method may include calculating a melanin correction value based on the melanin index, a reference melanin index, and a correction ratio. The correcting the first reflectance value may include correcting the first reflectance based on the melanin correction value.

The correction ratio may include a rate of change of the first reflectance value as compared to a change in the melanin index.

The method may include calculating a hemoglobin correction value based on the hemoglobin index, a reference hemoglobin index, and a correction ratio. The correcting the target component value may include correcting the target component value based on the hemoglobin correction value.

The correction ratio may include a rate of change of a residual, which is a value obtained by subtracting a trend line from the target component value, as compared to a change in the hemoglobin index.

The obtaining of the spectrum may include emitting, by a light source part, light in a predetermined wavelength range onto the object; and splitting, by a spectrometer, the light scattered or reflected from the object.

The estimating of the target component value may include estimating the target component value based on absorbance values in a first wavelength range of the predetermined wavelength range.

The method may include converting the first reflectance value into a first absorbance value; and estimating the melanin index and the hemoglobin index based on the first absorbance value.

The estimating of the melanin index and the hemoglobin index may include estimating the melanin index based on absorbance values in a second wavelength range of the predetermined wavelength range associated with melanin, and estimating the hemoglobin index based on absorbance values in a third wavelength range associated with hemoglobin.

The obtaining of the spectrum may include driving a first light source part to obtain a spectrum in a first wavelength range; driving a second light source part to obtain a spectrum in a second wavelength range associated with melanin; and driving a third light source part to obtain a spectrum in a third wavelength range associated with hemoglobin.

The method may include estimating the melanin index based on the spectrum in the second wavelength range; and estimating the hemoglobin index based on the spectrum in the third wavelength range. The obtaining of the second reflectance value may include obtaining the second reflectance value by correcting a first reflectance value of the spectrum in the first wavelength range based on the melanin index.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
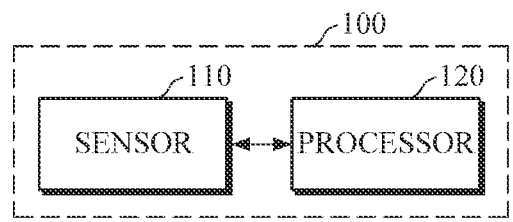
FIG. 1 is a block diagram illustrating an apparatus for estimating a target component according to an example embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of example embodiments are included in the following detailed description and drawings. Throughout the drawings and the detailed description, unless otherwise described, the same drawing reference numerals will be understood to refer to the same elements, features, and structures.

It will be understood that although terms "first," "second," etc. may be used herein to describe various elements, these elements should not be limited by these terms. These terms are only used to distinguish one element from another. Any references to singular forms of terms may include the plural forms of the terms unless expressly stated otherwise. In addition, unless explicitly described to the contrary, an expression such as "comprising" or "including" will be understood to imply the inclusion of stated elements but not the exclusion of any other elements. Also, terms such as "unit," "module," etc., should may refer to a unit that performs at least one function or operation and that may be embodied as hardware, software, or a combination thereof.

Hereinafter, example embodiments of an apparatus and method for estimating a target component will be described in detail with reference to the accompanying drawings. Various example embodiments of the apparatus for estimating a target component may be mounted in various types of wearable devices, such as a smartwatch worn on the wrist, a smart band-type wearable device, a headphone-type wearable device, a headband-type wearable device, etc., in mobile devices, such as a smartphone, a tablet personal computer (PC), etc., or in a system of a specialized medical institution. However, the apparatus for estimating a target component is not limited thereto.

FIG. 1 is a block diagram illustrating an apparatus for estimating a target component according to an example embodiment.

Referring to FIG. 1, the apparatus 100 for estimating a target component includes a sensor 110 and a processor 120.

The sensor 110 may emit light onto an object to estimate a target component from the object, and may obtain a spectrum of light scattered or reflected from the object (hereinafter referred to as a "reflection spectrum"). The object may be skin tissue of a human body and may be, for example, an upper part of the wrist that is adjacent to the radial artery or where veins or capillaries are located, a finger, and the like.

The processor 120 may control the sensor 110, and may estimate a target component based on the reflection spectrum obtained by the sensor 110. In this case, the target component may include carotenoid, blood glucose, sugar intake, triglyceride, cholesterol, calories, protein, in vivo body fluid, in vitro body fluid, uric acid, etc., but is not limited thereto. The following description will be given using carotenoid as an example.

The processor 120 may obtain absorbance based on the obtained reflection spectrum, and may estimate a target component based on the absorbance. In this case, the effects of hemoglobin and melanin pigment, responsible for skin color, are reflected in an absorbance spectrum, such that in order to stably estimate carotenoid from people of various skin colors, the effects of melanin pigment and hemoglobin may be eliminated in the process of estimating carotenoid using the absorbance spectrum.

Figure 2A:
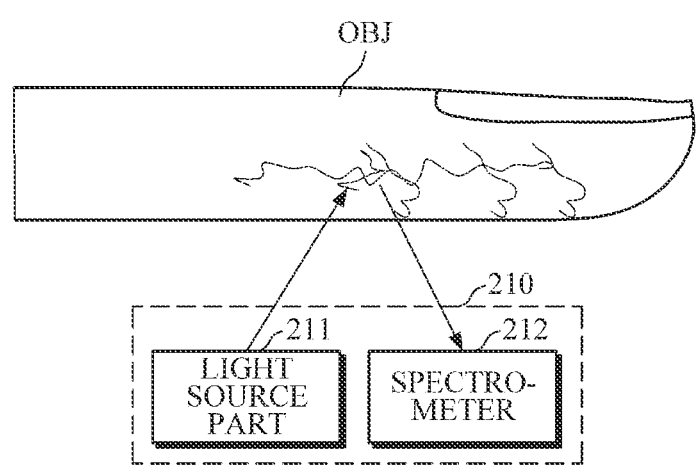
FIGS. 2A and 2B are diagrams explaining a configuration of a sensor according to example embodiments.
Figure 2B:
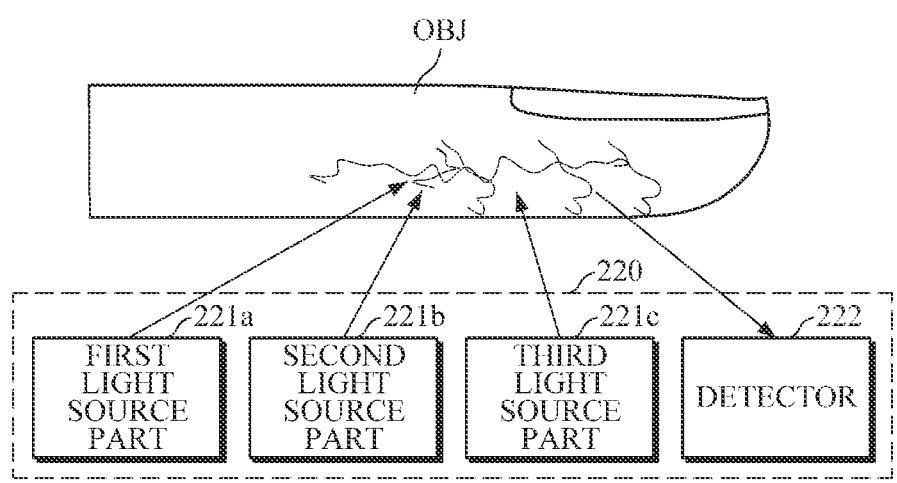

FIGS. 2A and 2B are diagrams explaining a configuration of a sensor according to example embodiments of the present disclosure. FIGS. 3A to 3D are diagrams explaining a process of estimating a target component by a processor 120 of FIG. 1.

Referring to FIG. 2A, a sensor 210 according to an example embodiment includes a light source part 211 and a spectrometer 212.

The light source part 211 may emit light in a predetermined wavelength range onto an object OBJ. The light source part may include a light emitting diode (LED), a laser diode (LD), a phosphor, and the like, but is not limited thereto. The spectrometer 212 may obtain a reflection spectrum by splitting scattered or reflected light when light, emitted by the light source part 211, is scattered or reflected from the object OBJ.

Here, the predetermined wavelength range may include a wavelength range associated with a target component (hereinafter referred to as a "first wavelength range"), a wavelength range associated with melanin (hereinafter referred to as a "second wavelength range") for eliminating the effect of melanin pigment so as to accurately measure a peak of a target component in the first wavelength range, and a wavelength range associated with hemoglobin (hereinafter referred to as a "third wavelength range") for eliminating the effect of hemoglobin. For example, the predetermined wavelength range may include a relatively wide wavelength range of visible light such as, for example, a wavelength range of 400 nm to 700 nm, so as to include all of the first wavelength range of, for example, 470 nm to 510 nm, the second wavelength range of, for example, 400 nm to 470 nm, and the third wavelength range of, for example, 530 nm to 590 nm.

Based on the sensor 210 obtaining the reflection spectrum in the predetermined wavelength range, the processor 120 may convert reflectance at each wavelength (hereinafter referred to as a "first reflectance") of the obtained spectrum into absorbance (hereinafter referred to as a "first absorbance"). A relational expression, as represented by the following Equation 1, is an example of a function expression for converting reflectance into absorbance.

$$\mathrm{Abs}(\lambda) = -\log_{10}\left(\frac{\mathrm{Re}(\lambda)}{100}\right) \quad \text{[Equation 1]}$$

Herein, Abs($\lambda$) denotes the first absorbance at the wavelength of $\lambda$, and Re($\lambda$) denotes the first reflectance at the wavelength of $\lambda$.

Based on obtaining the first absorbance, the processor 120 may obtain a melanin index (MI) and a hemoglobin index (HbI) based on the first absorbance, so as to eliminate the effect of melanin and the effect of hemoglobin. For example, the processor 120 may obtain the MI and the HbI by using the following Equations 2 and 3.

$$MI = \sum_i a_i \mathrm{Abs}_i \quad \text{[Equation 2]}$$

Herein, MI denotes the melanin index, $\mathrm{Abs}_i$ denotes absorbance at the wavelength of i, and $a_i$ denotes a coefficient. In this case, the wavelength i may denote each wavelength in the second wavelength range associated with melanin. That is, the processor 120 may obtain the MI by using wavelengths in the second wavelength range of the predetermined wavelength range. However, the processor 120 is not limited thereto, and may use the first absorbance values of the entire predetermined wavelength range.

$$HbI = \sum_i b_i \mathrm{Abs}_i \quad \text{[Equation 3]}$$

Herein, HbI denotes the hemoglobin index, $\mathrm{Abs}_i$ denotes absorbance at the wavelength of i, and $b_i$ denotes a coefficient. In this case, the wavelength i may denote each wavelength in the third wavelength range associated with hemoglobin. That is, the processor 120 may obtain the HbI by using wavelengths in the third wavelength range of the predetermined wavelength range. However, the processor 120 is not limited thereto, and may use the first absorbance values of the entire predetermined wavelength range.

The processor 120 may obtain a corrected reflectance (hereinafter referred to as a "second reflectance"), by correcting the first reflectance based on the MI. In this case, in order to compensate for a change in the MI, which has different effects on the spectrum at each wavelength, the processor 120 may compensate for the obtained MI based on a reference melanin index, and may calculate a melanin correction value by applying a correction ratio. The processor 120 may obtain the second reflectance by applying the calculated melanin correction value to the first reflectance. The following Equation 4 is an example of a function expression for obtaining the second reflectance from the first reflectance based on the MI.

$$\mathrm{Re}_M(\lambda) = \mathrm{Re}(\lambda) + (MI - \alpha) * (-f(\lambda)) \quad \text{[Equation 4]}$$

$$f(\lambda) = \frac{\partial \text{Re}(MI, \lambda)}{\partial MI}$$

Figure 3A:
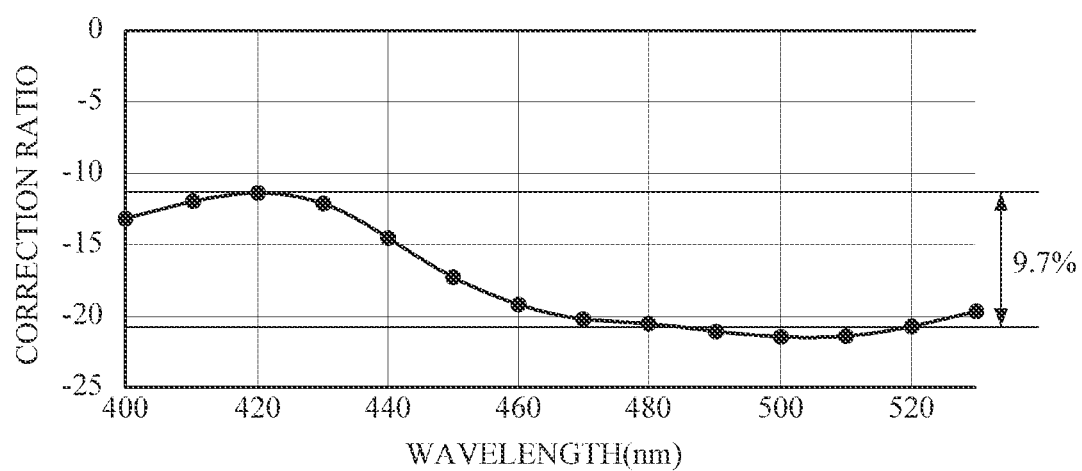
FIGS. 3A to 3D are diagrams explaining a process of estimating a target component according to an example embodiment.
Figure 3B:
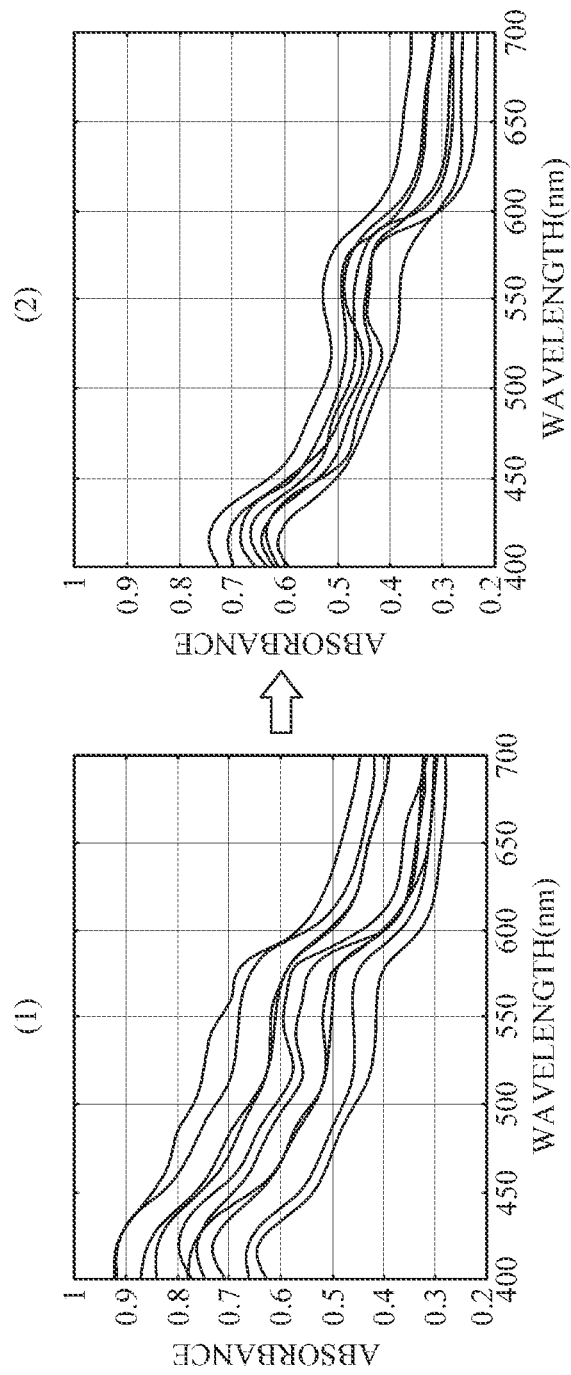

Herein, $\text{Re}_M(\lambda)$ denotes the first reflectance at the wavelength of $\lambda$; $\text{Re}_{M'}(\lambda)$ denotes the second reflectance at the wavelength of $\lambda$; MI denotes the melanin index obtained based on the first absorbance; $\alpha$ denotes the reference melanin index used for compensating for the change in the MI, which has different effects on the spectrum at each wavelength; $f(\lambda)$ denotes the correction ratio that may correspond to a rate of change of the first reflectance according to a change in the MI at each wavelength. FIG. 3A is a diagram illustrating a graph of a correction ratio obtained using an in vivo spectrum. As illustrated in FIG. 3A, there is a difference in the rate of change of reflectance according to a change in the MI for each wavelength. FIG. 3B is a diagram illustrating an absorbance spectrum obtained before the effect of melanin is reflected, and an absorbance spectrum obtained after the effect of melanin is reflected.

Further, based on obtaining the second reflectance, from which the effect of melanin is eliminated based on the MI, the processor 120 may convert the second reflectance at each wavelength into absorbance at each wavelength (hereinafter referred to as a "second absorbance"). The following Equation 5 is an example of a function expression for obtaining the second absorbance.

$$\text{Abs}_M(\lambda) = -\log_{10}\left(\frac{\text{Re}_M(\lambda)}{100}\right) \quad \text{[Equation 5]}$$

Herein, $\text{Abs}_M(\lambda)$ denotes the second absorbance at the wavelength of $\lambda$, and $\text{Re}_{M'}(\lambda)$ denotes the second reflectance at the wavelength of $\lambda$.

Based on obtaining the second absorbance, the processor 120 may obtain a target component by using the second absorbance. For example, the processor 120 may obtain an estimated carotenoid value by using the following Equation 6.

$$CI = \sum_i c_i \text{Abs}_{M,i} \quad \text{[Equation 6]}$$

Herein, CI denotes a carotenoid value; $c_i$ denotes a coefficient; and $\text{Abs}_{M,i}$ denotes the second absorbance obtained by compensating for the effect of melanin pigment at the wavelength of i. In this case, i denotes each wavelength of the first wavelength range in the predetermined wavelength range. However, the wavelength is not limited thereto, and may include all of the wavelengths of the absorbance spectrum or at least three peak wavelengths selected from the first wavelength range.

Based on obtaining the estimated target component value as described above, the processor 120 may compensate for the effect of hemoglobin by using the HbI. Hemoglobin generally causes a carotenoid content to be biased to a smaller value, such that the processor 120 may compensate for the effect of hemoglobin in the estimated target component value.

Figure 3C:
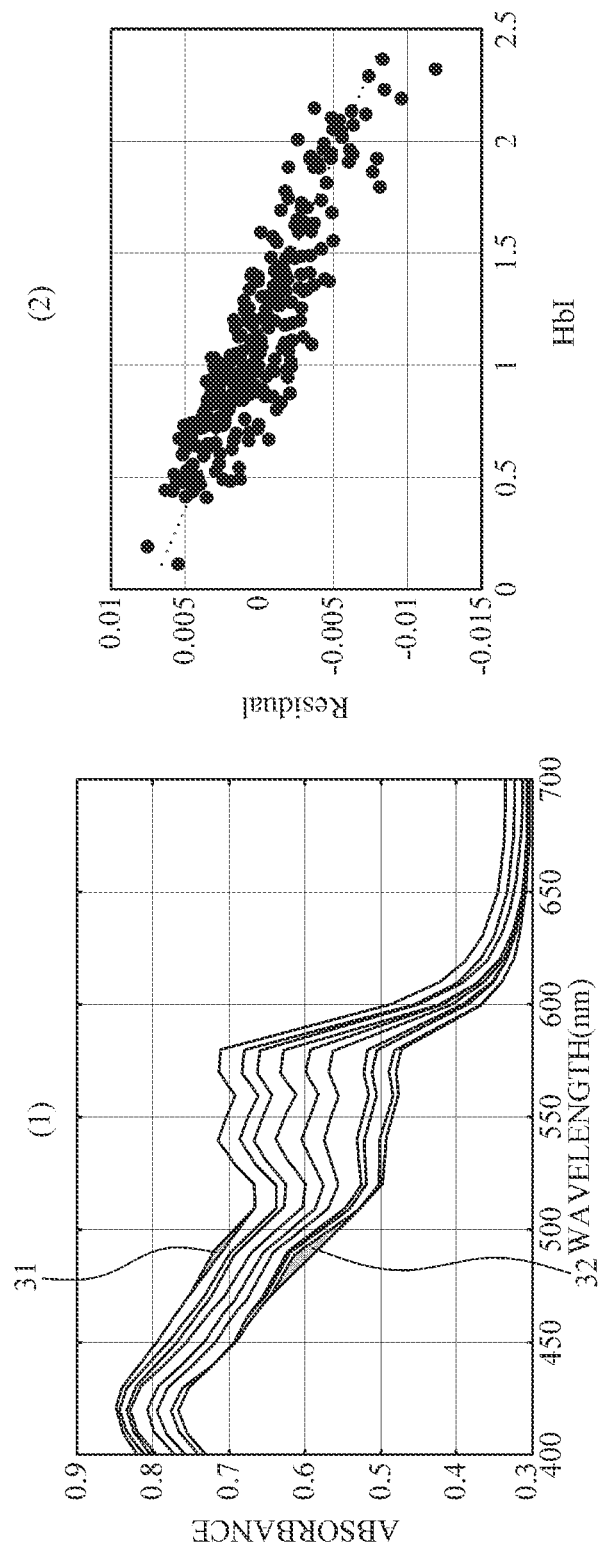

In FIG. 3C, (1) illustrates absorbance spectra according to a change in pressure exerted on the object when the object applies a pressing force to the sensor 110, in which an upper spectrum is obtained at a relatively low pressure, and a lower spectrum is obtained at a relatively high pressure. That is, as pressure decreases, a volume of blood flowing in the blood vessels of the object increases, such that absorbance increases due to hemoglobin; by contrast, as pressure increases, a volume of blood decreases, such that absorbance decreases due to hemoglobin. Accordingly, a wavelength range 31 of 470 nm to 510 nm of the uppermost spectrum, a signal for detecting carotenoid is relatively low; and in a wavelength range 32 of 470 nm to 510 nm of the lowermost spectrum, a signal for detecting carotenoid is relatively high. In FIG. 3C, (2) illustrates an example in which as the HbI increases, a residual of carotenoid is biased negatively.

The processor 120 may normalize the HbI by using a reference hemoglobin index, and may calculate a hemoglobin correction value by applying a correction ratio to the normalized value. In addition, the processor 120 may correct the target component by applying the calculated hemoglobin correction value to the estimated target component value. The following Equation 7 is an example of a function expression for compensating for the effect of hemoglobin in the estimated target component value.

$$CI_{comp} = CI + \gamma \times (HbI - \beta) \times g(\lambda) \quad \text{[Equation 7]}$$

$$g(\lambda) = -\frac{\partial \text{Residual}}{\partial Hbi}$$

Herein, $CI_{comp}$ denotes the corrected carotenoid; HbI denotes the hemoglobin index; $\beta$ denotes the reference hemoglobin index; $g(\lambda)$ denotes a correction ratio, including a rate of change in residual compared to a change in the hemoglobin index. In this case, the residual is a value obtained by subtracting a trend line from the estimated target component value, and tends to be biased negatively as the hemoglobin index increases; and $\gamma$ denotes a predetermined reflection rate of compensation.

Figure 3D:
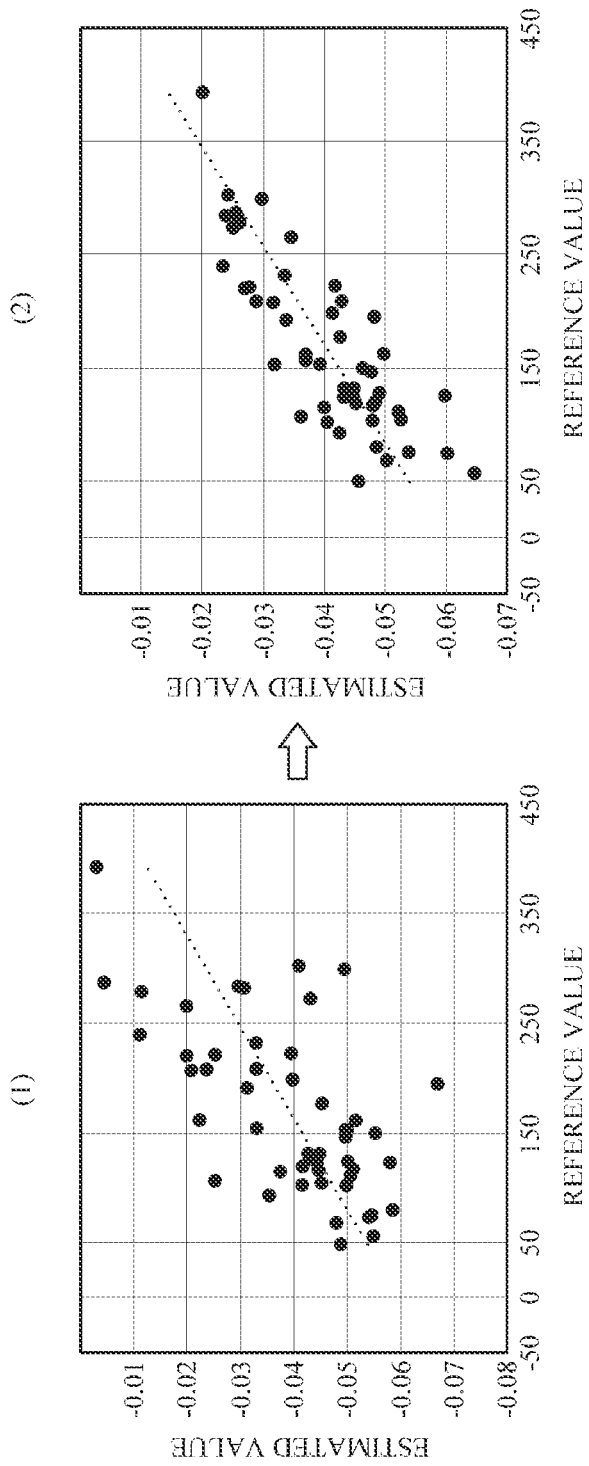

In FIG. 3D, (1) illustrates dispersion of the estimated carotenoid values, from which the effect of melanin is eliminated; and (2) illustrates dispersion of the carotenoid values, from which the effect of hemoglobin is eliminated, as well as the effect of melanin. As illustrated in FIG. 3D, it can be seen that by eliminating the effect of hemoglobin, accuracy of the estimated carotenoid values may be further improved.

FIG. 2B is a diagram explaining a configuration of a sensor according to another example embodiment of the present disclosure.

Referring to FIG. 2B, the sensor 220 according to another embodiment includes: a first light source part 221a for emitting light in the first wavelength range, a second light source part 221b for emitting light in the second wavelength range; a third light source part 221c for emitting light in the third wavelength range; and a detector 222 for detecting scattered or reflected light when light at each wavelength, emitted by the respective light sources 221a, 221b, and 221c, is scattered or reflected, so as to obtain spectra.

The first light source part 221a, the second light source part 221b, and the third light source part 221c may include one or more light sources. In this case, the light source may include a light emitting diode (LED), a laser diode (LD), a phosphor, and the like, but is not limited thereto. The detector 222 may include one or more photo diodes, one or more photo diode arrays, a complementary metal-oxide semiconductor (CMOS) image sensor, a charge-coupled device (CCD) image sensor, and the like.

The first light source part 221a may include one or more light sources, each of which may emit light of a predetermined wavelength in the first wavelength range. Further, the second light source part 221b may include one or more light sources, each of which may emit light of a predetermined wavelength in the second wavelength range. Further still, the third light source part 221c may include one or more light sources, each of which may emit light of a predetermined wavelength in the third wavelength range.

The processor 120 may determine wavelengths of light sources to be driven among the first light source part 221a, the second light source part 221b, and the third light source part 221c, and the processor 120 may sequentially or simultaneously drive light sources of the determined wavelengths. For example, the processor 120 may select at least three light sources such as, for example, light sources of the wavelengths of 470 nm, 490 nm, and 510 nm, from the first light source part 221a, may select at least one light source in a wavelength range of 400 nm to 470 nm, having relatively high accuracy of melanin index estimation, from the second light source part 221b, and may select at least one light source in a wavelength range of 530 nm to 590 nm, having relatively high accuracy of hemoglobin estimation, from the third light source part 221c. The processor 120 may drive the selected light sources by sequentially or simultaneously turning on the respective light sources. However, driving of the light sources is not limited thereto, and the light sources may be driven with various patterns, such as by simultaneously driving the light sources in the respective light source parts 221a, 221b, and 221c, while sequentially driving the respective light source parts 221a, 221b, and 221c, and the like.

For example, the processor 120 may convert reflectance of the spectrum in the second wavelength range, which is obtained by driving the second light source part 221b, into absorbance, and may obtain the MI based on the absorbance as described above. Further, the processor 120 may convert reflectance of the spectrum in the third wavelength range, which is obtained by driving the third light source part 221c, into absorbance, and may obtain the HbI based on the absorbance. As described above, the processor 120 may correct reflectance of the spectrum, which is obtained by driving the first light source part 221a, based on the MI, may estimate a target component based on the corrected reflectance, and may obtain a final estimated target component value by correcting the target component based on the HbI.

In another example, the processor 120 may extract characteristic points based on spectra, obtained by the first light source part 221a, the second light source part 221b, and the third light source part 221c, in the respective wavelength ranges, and may estimate a target component based on the extracted characteristic points by using a pre-defined target component estimation model. In this case, the characteristic points may include reflectance values of spectra and absorbance values obtained by converting the reflectance values. However, the characteristic points are not limited thereto, and may include various combinations of the reflectance values and/or the absorbance values, such as a mean value of the reflectance values, a mean value of the absorbance values, and the like. In this case, the target component estimation model may be generated based on linear regression, non-linear regression, artificial neural networks, and the like.

Figure 4:
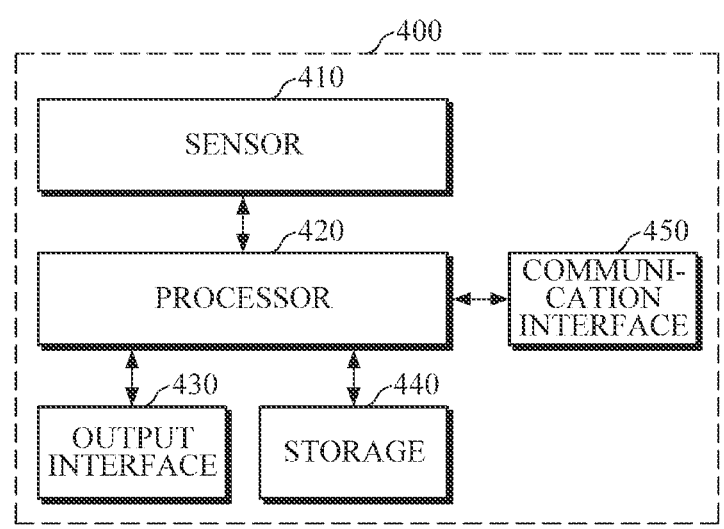
FIG. 4 is a block diagram illustrating an apparatus for estimating a target component according to another example embodiment.

FIG. 4 is a block diagram illustrating an apparatus for estimating a target component according to another example embodiment of the present disclosure.

Referring to FIG. 4, the apparatus 400 for estimating a target component includes a sensor 410, a processor 420, an output interface 430, a storage 440, and a communication interface 450. In this case, the sensor 410 and the processor 420 are described above in detail, such that the following description will be focused on non-overlapping parts.

The output interface 430 may output the spectrum, obtained by the sensor 410, and/or a variety of information processed by the processor 420 such as the MI, HbI, estimated target component values, and the like. The output interface 430 may include a visual output module such as a display, and the like, a voice output module such as a speaker, and the like, or a haptic module using vibrations, tactile sensation, and the like. In this case, the output interface 430 may divide a display area into two or more areas, and may display the estimated target component value in a first area, and may display detailed information related to the target component such as spectrum, MI, HbI, health condition, and the like, in a second area.

The storage 440 may store user information and reference information for estimating a target component, such as criteria for driving light sources, a target component estimation model, and the like. Further, the storage 440 may store a variety of information obtained, generated, and processed by the sensor 410 and/or the processor 420.

The storage 440 may include at least one storage medium of a flash memory type memory, a hard disk type memory, a multimedia card micro type memory, a card type memory (e.g., a secure digital (SD) memory, an eXtreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 450 may communicate with an external device through wired or wireless communication to receive various data from the external device. In this case, the external device may include an information processing device such as a smartphone, a tablet PC, a desktop computer, a laptop computer, and the like, but is not limited thereto.

For example, the communication interface 450 may receive a request for measuring a spectrum from an external device, and may transmit the received request to the processor 420. The communication interface 450 may receive reference information, such as a light source driving condition, an estimation model, etc., from the external device. In addition, the communication interface 450 may transmit a variety of information obtained, generated, and processed by the sensor 410 and/or the processor 420 to the external device.

In this case, the communication interface 450 may communicate with the external device by using various wired or wireless communication techniques, such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, 3G communication, 4G communication, 5G communication, and the like. However, the foregoing communication techniques are merely examples, and are not intended to be limiting.

Figure 5:
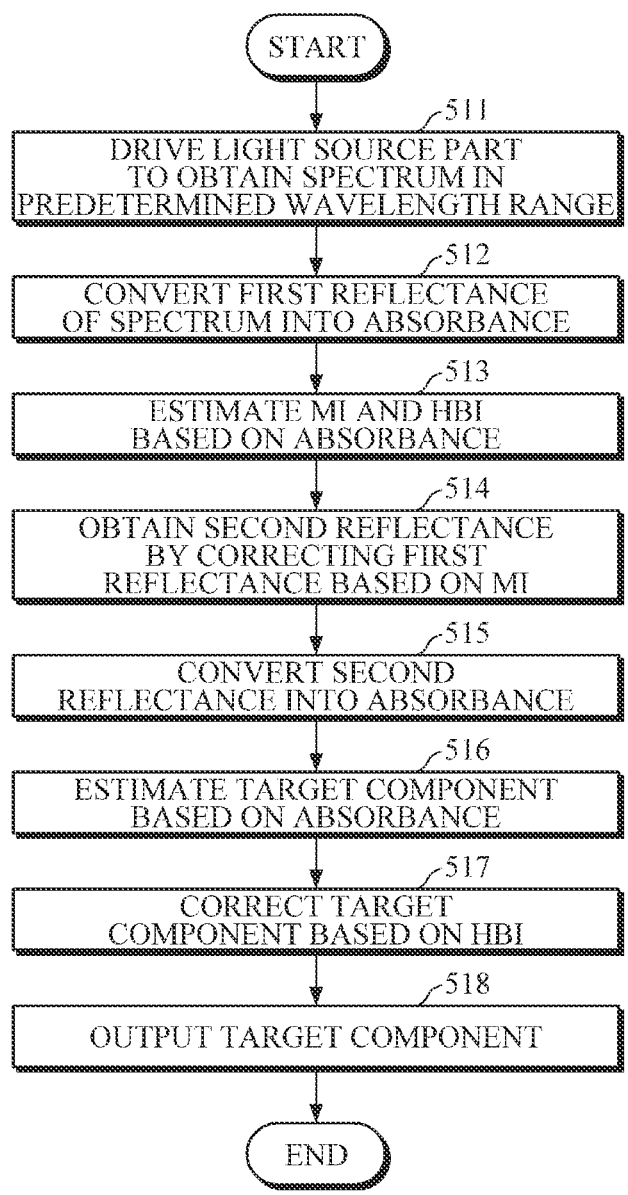
FIG. 5 is a flowchart illustrating a method of estimating a target component according to an example embodiment.

FIG. 5 is a flowchart illustrating a method of estimating a target component according to an example embodiment.

The method of FIG. 5 is an example of a method of estimating a target component according to the example embodiments of FIG. 1 or FIG. 4, which are described above in detail, and thus will be briefly described below.

First, the apparatus for estimating a target component may drive a light source part to emit light of a predetermined wavelength range, and may obtain a spectrum of light scattered or reflected from an object by using a spectrometer in operation 511. In this case, the predetermined wavelength range may include a relatively wide wavelength range such as, for example, a visible light range of 400 nm to 700 nm, so as to include an appropriate wavelength range for estimating melanin, hemoglobin, and a target component.

Then, the apparatus for estimating a target component may convert a first reflectance of the obtained spectrum into absorbance in operation 512, and may estimate MI and HbI based on the absorbance in operation 513.

Subsequently, the apparatus for estimating a target component may obtain a second reflectance by correcting the first reflectance based on the MI in operation 514, which is obtained by compensating for the effect of MI. In this case, in order to compensate for a change in spectrum at each wavelength according to a change in the MI, the apparatus for estimating a target component may normalize the MI based on a reference melanin index, and may obtain a melanin correction value by applying a correction ratio to the normalized MI. In addition, the apparatus for estimating a target component may obtain the second reflectance by applying the obtained melanin correction value to the first reflectance.

Next, the apparatus for estimating a target component may convert the second reflectance, obtained by compensating for the effect of melanin, into absorbance in operation 515, and may estimate a target component based on the absorbance in operation 516.

Then, the apparatus for estimating a target component may correct, in operation 517, the target component estimated in operation 516 based on the HbI obtained in operation 513. For example, the apparatus for estimating a target component may normalize the HbI based on a reference hemoglobin index, and may calculate a hemoglobin correction value based on a pre-defined reflection rate of compensation, a correction ratio, and the like. Further, the apparatus for estimating a target component may correct the target component by using the calculated hemoglobin correction value.

Subsequently, the apparatus for estimating a target component may output and provide the corrected estimated target component value to a user in operation 518.

Figure 6:
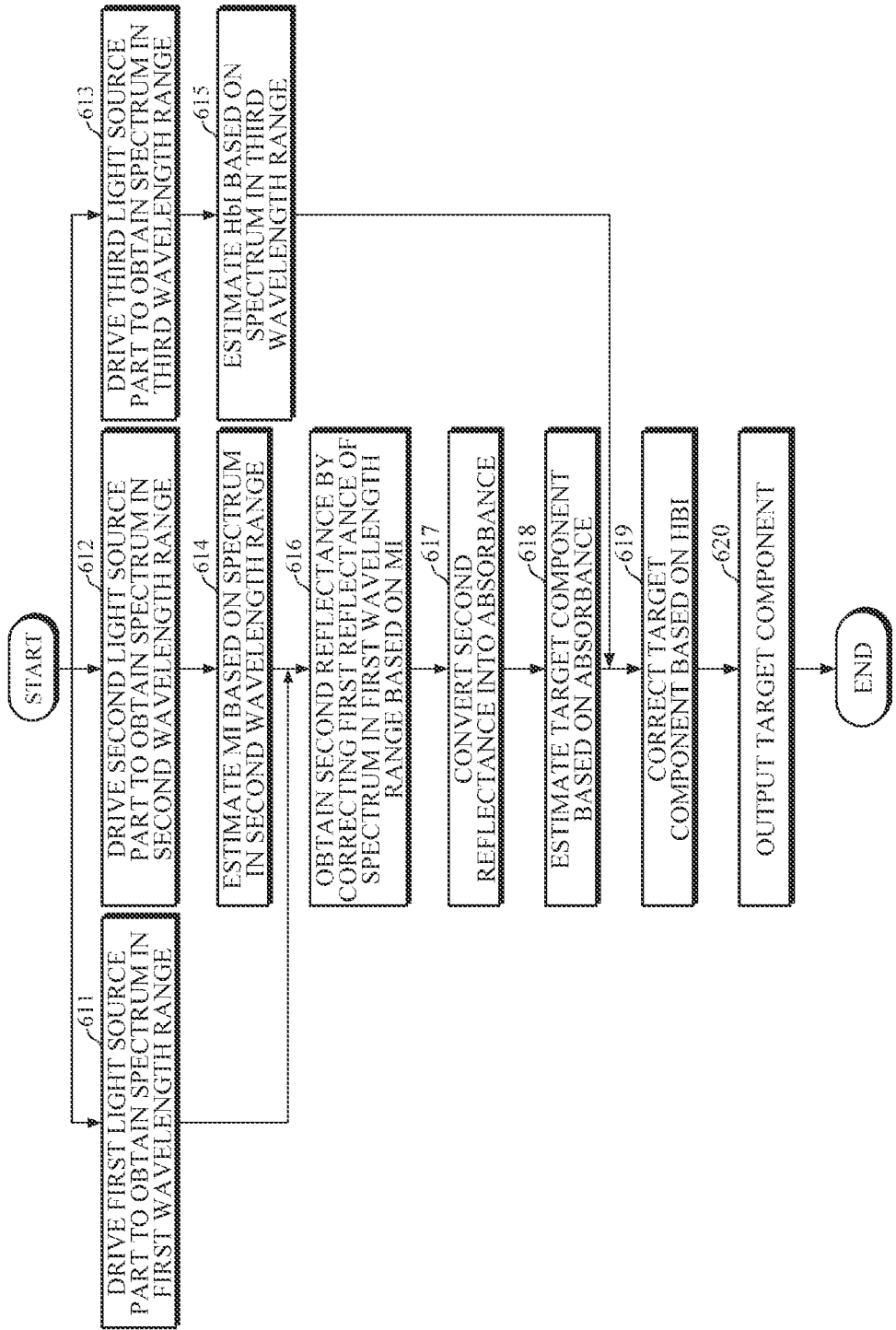
FIG. 6 is a flowchart illustrating a method of estimating a target component according to another example embodiment.

FIG. 6 is a flowchart illustrating a method of estimating a target component according to another example embodiment.

The method of FIG. 6 may be performed by the apparatuses 100 and 400 for estimating a target component according to the embodiments of FIG. 1 or FIG. 4.

Referring to FIG. 6, the apparatus for estimating a target component may drive the first light source part to obtain a spectrum in the first wavelength range in operation 611, may drive the second light source part to obtain a spectrum in the second wavelength range in operation 612, and may drive the third light source part to obtain a spectrum in the third wavelength range in operation 613. In this case, the first light source part, the second light source part, and the third light source part may be driven sequentially or simultaneously. Further, the first light source part may include one or more light sources emitting light in an appropriate wavelength range for estimating a target component such as, for example, a wavelength range of 470 nm to 510 nm; the second light source part may include one or more light sources emitting light in an appropriate wavelength range for estimating melanin such as, for example, a wavelength range of 400 nm to 470 nm; and the third light source part may include one or more light sources emitting light in an appropriate wavelength range for estimating hemoglobin such as, for example, a wavelength range of 530 nm to 590 nm.

Then, the apparatus for estimating a target component may estimate melanin index based on the spectrum in the second wavelength range in operation 614, and may estimate hemoglobin index based on the spectrum in the third wavelength range in operation 615.

Subsequently, the apparatus for estimating a target component may obtain a second reflectance in operation 616 by correcting the first reflectance of the spectrum obtained in operation 611 based on the MI.

Next, the apparatus for estimating a target component may convert the second reflectance into absorbance in operation 617, and may estimate a target component based on the absorbance in operation 618.

Then, the apparatus for estimating a target component may correct the target component based on the HbI to obtain a final estimated target component value in operation 619, and may output and provide the obtained estimated target component value to a user in operation 620.

Figure 7:
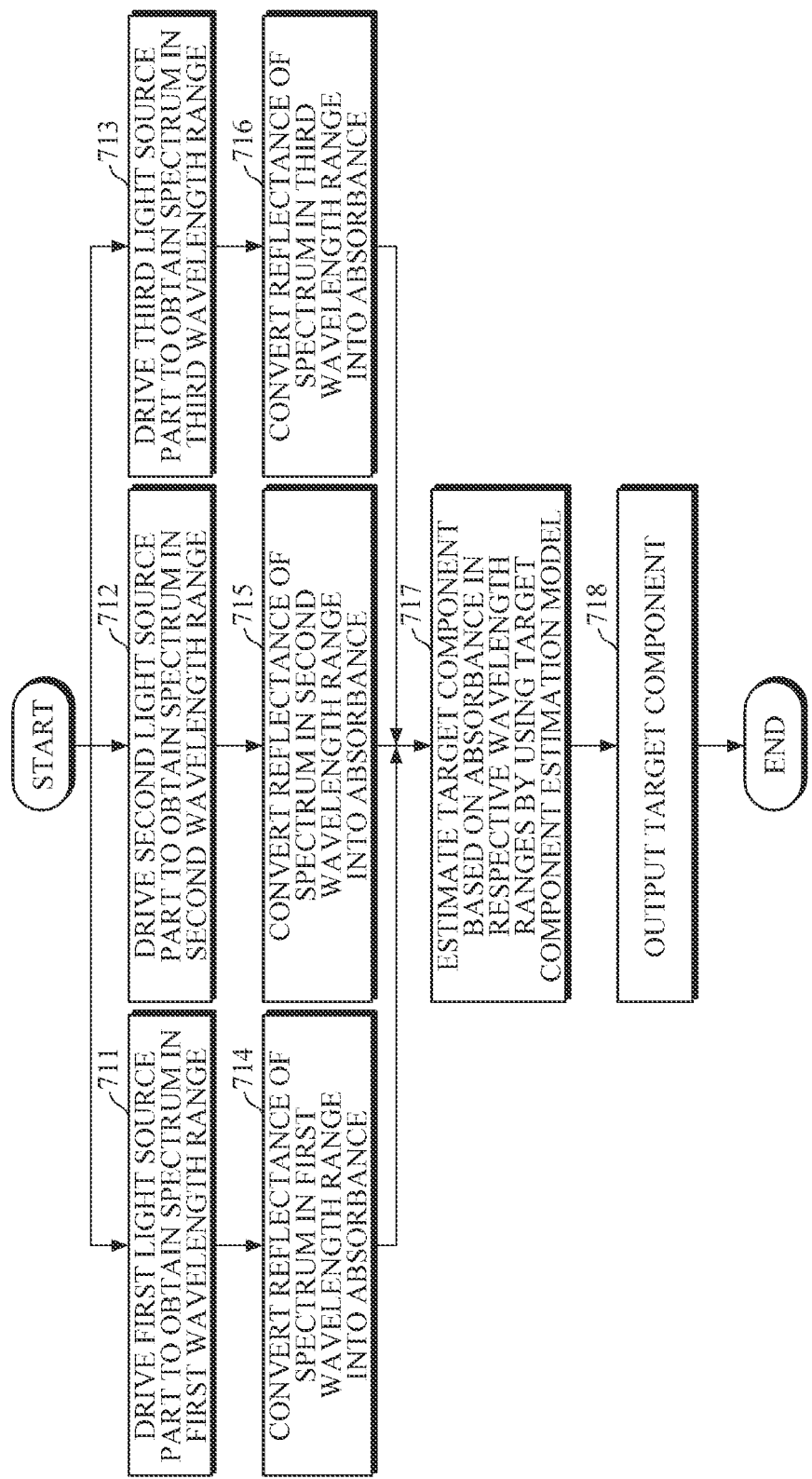
FIG. 7 is a flowchart illustrating a method of estimating a target component according to yet another example embodiment.

FIG. 7 is a flowchart illustrating a method of estimating a target component according to yet another example embodiment of the present disclosure. The method of FIG. 7 may be performed by the apparatuses 100 and 400 for estimating a target component according to the embodiments of FIG. 1 or FIG. 4.

Referring to FIG. 7, the apparatus for estimating a target component may drive the first light source part to obtain a spectrum in the first wavelength range in operation 711, may drive the second light source part to obtain a spectrum in the second wavelength range in operation 712, and may drive the third light source part to obtain a spectrum in the third wavelength range in operation 713. In this case, the first light source part, the second light source part, and the third light source part may be driven sequentially or simultaneously.

Then, the apparatus for estimating a target component may convert reflectance of the spectrum in the first wavelength range into absorbance in operation 714, may convert reflectance of the spectrum in the second wavelength range into absorbance in operation 715, and may convert reflectance of the spectrum in the third wavelength range into absorbance in operation 716.

Subsequently, the apparatus for estimating a target component may estimate a target component based on the absorbance in the respective wavelength ranges by using a target component estimation model in operation 717, and may output and provide the estimated target component value to a user in operation 718.

Figure 8:
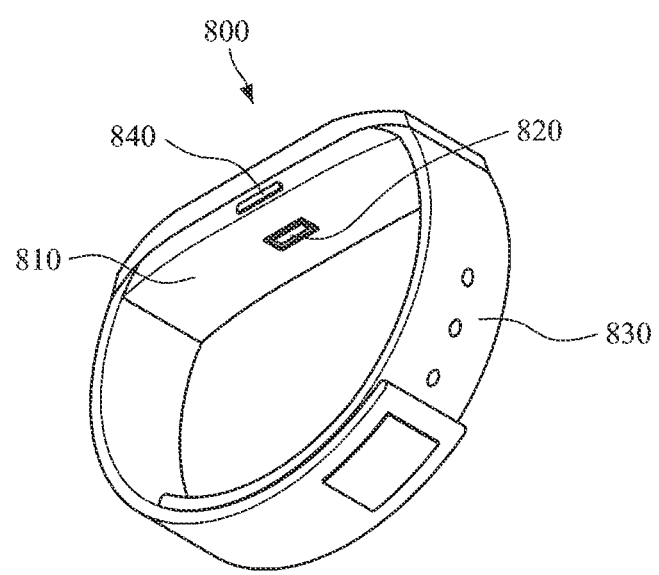
FIG. 8 is a diagram illustrating a wearable device according to an example embodiment.

FIG. 8 is a diagram illustrating a wearable device according to an example embodiment.

Although FIG. 8 illustrates a smart watch-type wearable device 800, the wearable device is not limited thereto, and may be modified in various shapes, such as a smart band, smart glasses, and the like. Further, the wearable device may be manufactured in the form of mobile devices such as a smartphone, a tablet PC, and the like. The aforementioned various embodiments of apparatuses 100 and 400 for estimating a target component may be mounted in the wearable device 800.

Referring to FIG. 8, the wearable device 800 includes a main body 810 and a strap 830.

The strap 830, which is connected to both ends of the main body 810, may be flexible so as to be wrapped around a user's wrist. The strap 830 may include a first strap and a second strap which are separated from each other. Respective ends of the first strap and the second strap are connected to the main body 810, and the other ends thereof may be connected to each other via a connecting means. In this case, the connecting means may be formed as magnetic connection, Velcro connection, pin connection, and the like, but is not limited thereto. Further, the strap 830 is not limited thereto, and may be integrally formed as a non-detachable band.

In this case, air may be injected into the strap 830, or the strap 830 may be provided with an air bladder to have elasticity according to a change in pressure applied to the wrist, and may transmit the change in pressure of the wrist to the main body 810.

A battery may be embedded in the main body 810 or the strap 830 to supply power to the wearable device 800.

The main body 810 may include a sensor 820 mounted on one side thereof. The sensor 820 may include a light source part and a spectrometer for detecting light in a predetermined wavelength range, or may include one or more light sources in wavelength ranges, associated with a target component, melanin, and hemoglobin, respectively, and a detector.

A processor may be mounted in the main body 810, and may be electrically connected to modules mounted in the wearable device 800. The processor may estimate a target component by compensating for the effects of melanin and hemoglobin in a spectrum measured by the sensor 820.

Furthermore, the main body 810 may include a storage which stores reference information for estimating a target component and information generated and processed by various modules thereof.

In addition, the main body 810 may include a manipulator 840 which is provided on one side surface of the main body 810, and receives a user's control command and transmits the received control command to the processor. The manipulator 840 may have a power button to input a command to turn on/off the wearable device 800.

Further, a display for outputting information to a user may be mounted on a front surface of the main body 810. The display may have a touch screen for receiving touch input. The display may receive a user's touch input and transmit the touch input to the processor, and may display processing results of the processor.

Moreover, the main body 810 may include a communication interface for communication with an external device. The communication interface may transmit a target component estimation result to the external device such as a user's smartphone.

The example embodiments may be implemented by computer-readable code written on a non-transitory computer-readable medium and that is executed by a processor. The non-transitory computer-readable medium may be any type of recording medium in which data is stored in a computer-readable manner.

Examples of the non-transitory computer-readable medium include a ROM, a RAM a CD-ROM, a magnetic tape, a floppy disc, an optical data storage, and a carrier wave (e.g., data transmission through the Internet). The non-transitory computer-readable medium can be distributed over a plurality of computer systems connected to a network so that computer-readable code is written thereto and executed therefrom in a decentralized manner. Functional programs, codes, and code segments for implementing the example embodiments can be deduced by programmers of ordinary skill in the art to which the present disclosure pertains.

The present disclosure has been described herein with regard to example embodiments. However, it will be obvious to those skilled in the art that various changes and modifications can be made without changing technical conception of the present disclosure. Thus, it is clear that the above-described embodiments are illustrative in all aspects and are not intended to limit the present disclosure.

What is claimed is:

1. An apparatus for estimating a target component value, the apparatus comprising:
   a sensor configured to obtain a spectrum of light scattered or reflected from an object; and
   a processor configured to:
      correct a first reflectance value of the spectrum based on a melanin index;
      obtain a second reflectance value based on correcting the first reflectance value;
      convert the second reflectance value into an absorbance value;
      estimate the target component value based on the absorbance value; and
      correct the target component value based on a hemoglobin index.

2. The apparatus of claim 1, wherein the processor is further configured to:
   calculate a melanin correction value based on the melanin index, a reference melanin index, and a correction ratio; and
   correct the first reflectance value based on the melanin correction value.

3. The apparatus of claim 2, wherein the correction ratio comprises a rate of change of the first reflectance value as compared to a change in the melanin index.

4. The apparatus of claim 2, wherein the processor is further configured to:
   calculate the melanin correction value by multiplying a value, obtained by subtracting the reference melanin index from the melanin index, by a negative of the correction ratio.

5. The apparatus of claim 1, wherein the processor is further configured to:
   calculate a hemoglobin correction value based on the hemoglobin index, a reference hemoglobin index, and a correction ratio; and
   correct the target component based on the hemoglobin correction value.

6. The apparatus of claim 5, wherein the correction ratio comprises a rate of change of a residual, which is a value obtained by subtracting a trend line from the target component value, as compared to a change in the hemoglobin index.

7. The apparatus of claim 5, wherein the processor is further configured to:
   calculate the hemoglobin correction value by multiplying a value, obtained by subtracting the reference hemoglobin index from the hemoglobin index, by a predetermined ratio, and multiplying a resulting value by the correction ratio.

8. The apparatus of claim 1, wherein the sensor comprises:
a light source part configured to emit light in a predetermined wavelength range onto the object; and
a spectrometer configured to split the light scattered or reflected from the object to obtain the spectrum.

9. The apparatus of claim 8, wherein the predetermined wavelength range comprises a wavelength range of visible light.

10. The apparatus of claim 8, wherein the processor is further configured to estimate the target component based on absorbance values in a first wavelength range of the predetermined wavelength range.

11. The apparatus of claim 8, wherein the processor is further configured to:
convert the first reflectance value into a first absorbance value; and
estimate the melanin index and the hemoglobin index based on the first absorbance value.

12. The apparatus of claim 11, wherein the processor is further configured to:
estimate the melanin index based on absorbance values in a second wavelength range of the predetermined wavelength range associated with melanin; and
estimate the hemoglobin index based on absorbance values in a third wavelength range associated with hemoglobin.

13. The apparatus of claim 1, wherein the sensor comprises:
a first light source part configured to emit light in a first wavelength range;
a second light source part configured to emit light in a second wavelength range associated with melanin;
a third light source part configured to emit light in a third wavelength range associated with hemoglobin; and
a detector configured to detect the light scattered or reflected from the object.

14. The apparatus of claim 13, wherein the processor is further configured to:
estimate the melanin index by driving the second light source part;
estimate the hemoglobin index by driving the third light source part; and
obtain the second reflectance value by correcting the first reflectance value of the spectrum, detected by driving the first light source part, based on the melanin index.

15. The apparatus of claim 13, wherein the first wavelength range includes a wavelength range of 470 nanometers (nm) to 510 nm, the second wavelength range includes a wavelength range of 400 nm to 470 nm, and the third wavelength range includes a wavelength range of 530 nm to 590 nm.

16. The apparatus of claim 13, wherein the detector comprises one or more of a photo diode, a complementary metal-oxide semiconductor (CMOS) image sensor, and a charge-coupled device (CCD) image sensor.

17. The apparatus of claim 1, wherein the target component value comprises one or more of a carotenoid value, a blood glucose value, a sugar intake value, a triglyceride value, a cholesterol value, a caloric value, a protein value, an in vivo body fluid value, an in vitro body fluid value, and a uric acid value.

18. An apparatus for estimating a target component value, the apparatus comprising:
a first light source part configured to emit light in a first wavelength range associated with a target component;
a second light source part configured to emit light in a second wavelength range associated with melanin;
a third light source part configured to emit light in a third wavelength range associated with hemoglobin;
a detector configured to detect light, scattered or reflected from an object, in the first wavelength range, the second wavelength range, and the third wavelength range; and
a processor configured to:
convert a first reflectance value of the light in the first wavelength range into a first absorbance value;
convert a second reflectance value of the light in the second wavelength range into a second absorbance value;
convert a third reflectance value of the light in the third wavelength range into a third absorbance value; and
estimate the target component value of the target component, based on the first absorbance value, the second absorbance value, and the third absorbance value.

19. The apparatus of claim 18, wherein the processor is further configured to:
sequentially or simultaneously drive the first light source part, the second light source part, and the third light source part.

20. A method of estimating a target component value, the method comprising:
obtaining a spectrum of light scattered or reflected from an object;
correcting a first reflectance value of the spectrum based on a melanin index;
obtaining a second reflectance value based on correcting the first reflectance value;
converting the second reflectance value into an absorbance value;
estimating the target component value based on the absorbance value; and
correcting the target component value based on a hemoglobin index.

21. The method of claim 20, further comprising:
calculating a melanin correction value based on the melanin index, a reference melanin index, and a correction ratio,
wherein the correcting the first reflectance value comprises correcting the first reflectance based on the melanin correction value.

22. The method of claim 21, wherein the correction ratio comprises a rate of change of the first reflectance value as compared to a change in the melanin index.

23. The method of claim 20, further comprising:
calculating a hemoglobin correction value based on the hemoglobin index, a reference hemoglobin index, and a correction ratio,
wherein the correcting the target component value comprises correcting the target component value based on the hemoglobin correction value.

24. The method of claim 23, wherein the correction ratio comprises a rate of change of a residual, which is a value obtained by subtracting a trend line from the target component value, as compared to a change in the hemoglobin index.

25. The method of claim 20, wherein the obtaining of the spectrum comprises:
emitting, by a light source part, light in a predetermined wavelength range onto the object; and
splitting, by a spectrometer, the light scattered or reflected from the object.

26. The method of claim 25, further comprising:
converting the first reflectance value into a first absorbance value; and
estimating the melanin index and the hemoglobin index based on the first absorbance value.

27. The method of claim 26, wherein the estimating of the melanin index and the hemoglobin index comprises:
estimating the melanin index based on absorbance values in a second wavelength range of the predetermined wavelength range associated with melanin, and estimating the hemoglobin index based on absorbance values in a third wavelength range associated with hemoglobin.

28. The method of claim 20, wherein the estimating of the target component value comprises estimating the target component value based on absorbance values in a first wavelength range of the predetermined wavelength range.

29. The method of claim 20, wherein the obtaining of the spectrum comprises:

driving a first light source part to obtain a spectrum in a first wavelength range;

driving a second light source part to obtain a spectrum in a second wavelength range associated with melanin; and driving a third light source part to obtain a spectrum in a third wavelength range associated with hemoglobin.

30. The method of claim 29, further comprising:

estimating the melanin index based on the spectrum in the second wavelength range; and estimating the hemoglobin index based on the spectrum in the third wavelength range, wherein the obtaining of the second reflectance value comprises obtaining the second reflectance value by correcting a first reflectance value of the spectrum in the first wavelength range based on the melanin index.

* * * * *